United States Patent
Zhang et al.

(10) Patent No.: US 7,429,584 B2
(45) Date of Patent: Sep. 30, 2008

(54) FURO[2.3-B]PYRIDINE DERIVATIVES FOR THE TREATMENT OF HYPER-PROLIFERATIVE DISORDERS

(75) Inventors: Chengzhi Zhang, Orange, CT (US); Gaetan Ladouceur, Guilford, CT (US); Michael J. Burke, New Haven, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 281 days.

(21) Appl. No.: 10/515,605

(22) PCT Filed: Jul. 11, 2003

(86) PCT No.: PCT/US03/21688

§ 371 (c)(1), (2), (4) Date: Nov. 23, 2004

(87) PCT Pub. No.: WO2004/007502

PCT Pub. Date: Jan. 22, 2004

(65) Prior Publication Data

US 2006/0040960 A1    Feb. 23, 2006

Related U.S. Application Data

(60) Provisional application No. 60/395,065, filed on Jul. 11, 2002.

(51) Int. Cl.
| | |
|---|---|
| *C07D 491/048* | (2006.01) |
| *C07D 413/06* | (2006.01) |
| *C07D 401/06* | (2006.01) |
| *A61K 31/4355* | (2006.01) |
| *A61K 31/496* | (2006.01) |
| *A61K 31/5377* | (2006.01) |
| *A61P 35/04* | (2006.01) |
| *C07D 491/14* | (2006.01) |
| *A61K 31/519* | (2006.01) |

(52) U.S. Cl. .............. 514/233.8; 544/127; 544/278; 546/115; 546/89; 514/254.11; 514/302; 514/260.1

(58) Field of Classification Search .............. 544/127; 546/115; 514/233.8, 302
See application file for complete search history.

(56) References Cited

U.S. PATENT DOCUMENTS 6,096,749 A    8/2000   Traxler et al. ............... 514/258

FOREIGN PATENT DOCUMENTS

| DE | 107287 | * 7/1974 |
|---|---|---|
| EP | 0459611 | 12/1991 |
| WO | 0102409 | 1/2001 |

OTHER PUBLICATIONS

Gewald, V. K., et al., "3-Amino-furo[2.3-b]pyridine", Journal Fur Praktische Chemie, 318(2): 313-320 (1976).

* cited by examiner

*Primary Examiner*—Brenda Coleman
*Assistant Examiner*—Susanna Moore
(74) *Attorney, Agent, or Firm*—Edwards Angell Palmer & Dodge LLP; Barry Kramer; Ralph A. Loren

(57) ABSTRACT

This invention relates to a compound of Formula (I) wherein Y is CH or N; $Ar^1$ is phenyl or pyridyl each optionally substituted with 1 or 2 substituents each selected independently from $(C_1\text{-}C_3)$alkoxy halo, OH, $CF_3$, CN, $NO_2$ and $(C_1\text{-}C_3)$ alkyl, said alkyl being optionally substituted with $CF_3$; $Ar^2$ is phenyl or pyridyl each optionally substituted with 1 or 2 substituents each independently selected from halo, OH, CN, $NO_2$, $CF_3$, $(C_1\text{-}C_6)$alkoxy, $NR^1R^1$, $S(O)_2R^2$, $C(O)R^3$, and $(C_1\text{-}C_6)$alkyl optionally substituted with $R^4$, and its use in treating hyper-proliferative disorders.

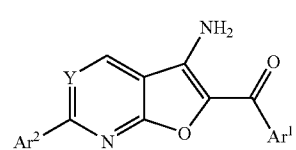

(I)

10 Claims, No Drawings

FURO[2.3-B]PYRIDINE DERIVATIVES FOR THE TREATMENT OF HYPER-PROLIFERATIVE DISORDERS

This patent application claims priority to U.S. Provisional Application 60/395,065 filed on Jul. 11, 2002.

FIELD OF THE INVENTION

This invention relates to novel furopyridine and furopyrimidine compounds, pharmaceutical compositions containing such compounds, and the use of those compounds or compositions for treating hyper-proliferative disorders.

DESCRIPTION OF THE INVENTION

One embodiment of this invention is a compound of Formula I

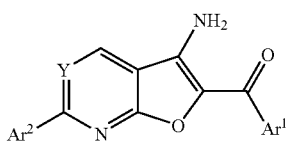

(I)

wherein
Y is CH or N;
$Ar^1$ is phenyl or pyridyl each optionally substituted with 1 or 2 substituents each being independently selected from ($C_1$-$C_3$)alkoxy, halo, OH, $CF_3$, CN, $NO_2$ and ($C_1$-$C_3$)alkyl, said alkyl being optionally substituted with $CF_3$;
$Ar^2$ is phenyl or pyridyl each optionally substituted with 1 or 2 substituents each being independently selected from halo, OH, CN, $NO_2$, $CF_3$, ($C_1$-$C_6$)alkoxy, $NR^1R^1$, $S(O)_2$ $R^2$, $C(O)R^3$, and ($C_1$-$C_6$)alkyl optionally substituted with $R^4$;
$R^1$ is selected from H, $S(O)_2N[(C_1$-$C_3$)alkyl$]_2$, $S(O)_2NH(C_1$-$C_3$)alkyl, $C(O)(C_1$-$C_3$)alkyl where said alkyl is optionally substituted with $NR^5R^5$, and ($C_1$-$C_3$)alkyl where said alkyl is optionally substituted with 1 or 2 substituents each selected independently from OH and ($C_1$-$C_3$)alkoxy, with the proviso that in any $NR^1R^1$ group when one $R^1$ is $S(O)_2$ $N[(C_1$-$C_3$)alkyl$]_2$, $S(O)_2NH(C_1$-$C_3$)alkyl or $C(O)(C_1$-$C_3$) alkyl then the other $R^1$ must be other than $S(O)_2N[(C_1$-$C_3$) alkyl$]_2$, $S(O)_2NH(C_1$-$C_3$)alkyl or $C(O)(C_1$-$C_3$)alkyl;
$R^2$ is selected from ($C_1$-$C_3$)alkyl, pyrrolidinyl, and $NH(C_1$-$C_3$)alkyl where said alkyl is optionally substituted with OH;
$R^3$ is selected from ($C_1$-$C_3$)alkyl, ($C_1$-$C_3$)alkoxy, morpholinyl, pyrrolidinyl, piperidinyl, and $NH(C_1$-$C_3$)alkyl where said alkyl is optionally substituted with OH, ($C_1$-$C_3$)alkoxy or $N[(C_1$-$C_3$)alkyl$]_2$;
$R^4$ is selected from OH, CN, $CF_3$, ($C_1$-$C_3$)alkoxy, C(O) $NR^5R^5$, $NR^5R^5$, and piperidinyl; and
$R^5$ is selected from H, ($C_1$-$C_3$)alkyl, $C(O)(C_1$-$C_3$)alkyl, $S(O)_2$ ($C_1$-$C_3$)alkyl and piperidinyl, with the proviso that in any $NR^5R^5$ group when one $R^5$ is $C(O)(C_1$-$C_3$)alkyl or $S(O)_2$ ($C_1$-$C_3$)alkyl, then the other $R^5$ must be other than $C(O)$ ($C_1$-$C_3$)alkyl or $S(O)_2(C_1$-$C_3$)alkyl; and
excluding (3-amino-6-phenylfuro[2,3b]pyridin-2-yl)(phenyl)methanone, (3-amino6-phenylfuro[2,3b]pyridin-2-yl) (4nitrophenyl)methanone, and (3-amino6-(4-methylphenyl)furo[2,3-b]pyridin-2-yl)(phenyl)methanone, or a pharmaceutically acceptable salt thereof.

The terms identified above have the following meaning throughout:

The term "optionally substituted" means that the moiety so modified may have from none to up to at least the highest number of substituents indicated. A substituent may replace any H atom on the moiety so modified as long as the replacement is chemically possible and chemically stable. When there are two or more substituents on any moiety, each substituent is chosen independently of any other substituent and can, accordingly, be the same or different.

The terms "($C_1$-$C_3$)alkyl" and "($C_1$-$C_6$)alkyl" mean a linear or branched saturated carbon group having from 1 to about 3 or about 6 C atoms, respectively. Such groups include but are not limited to methyl, ethyl, n-propyl, isopropyl, n-butyl, isobutyl, sec-butyl, tert-butyl, and the like.

The terms "($C_1$-$C_3$)alkoxy" and "($C_1$-$C_6$)alkoxy" mean a linear or branched saturated carbon group having from 1 to about 3 or about 6 C atoms, respectively, said carbon group being attached to an O atom. The O atom is the point of attachment of the alkoxy substituent to the rest of the molecule. Such groups include but are not limited to methoxy, ethoxy, n-propoxy, isopropoxy, n-butoxy, isobutoxy, sec-butoxy, tert-butoxy, and the like.

The term "halo" means an atom selected from Cl, Br, F.

When $Ar^1$ and/or $Ar^2$ is pyridyl, the pyridyl ring(s) may be attached to the core molecule at any available C atom.

When any R group or any substituent is pyrrolidinyl, piperidinyl, or morpholinyl, the ring may be attached to the rest of the molecule through any available C or N atom.

$NR^1R^1$ and $NR^5R^5$ in each instance means that each $R^1$ group or $R^5$ group, respectively, is selected independently from the other so that they may be the same or they may be different. Also, in each $N[(C_1$-$C_3$)alkyl$]_2$ group, each of the two alkyl groups is selected independently from the other so that they may be the same or they may be different.

When (O) is in a formula, it means =O; that is, an oxygen atom double bonded to the C atom to which it is attached.

When a phenyl or a pyridyl ring is substituted with one or more substituent, the substituent(s) may be attached to the phenyl ring at any available C atom. When there is more than 1 substituent on a ring, each is selected independently from the other so that they may be the same or different.

Representative compounds of Formula I are shown in Table 2.

TABLE 1

Fused furopyridines (Ia)

| Example No. | X | Ar | HPLC/ES-MS* [M + H]+ ($R_t$, min) |
|---|---|---|---|
| 1 | $CH_2$ | | 353.1 (2.87) |

TABLE 1-continued

Fused furopyridines (Ia)

| Example No. | X | Ar | HPLC/ES-MS* [M + H]+ (R$_t$, min) |
|---|---|---|---|
| 2 | CH$_2$ | 3-methyl-4-pyridyl (CH$_3$ at 4, attachment at 3) | 308.2 (2.26) |
| 3 | CH$_2$ | 2,4-dichlorophenyl | 361.2 (3.40) |
| 4 | CH$_2$ | 3-CF$_3$-4-pyridyl | 362.2 (2.89) |
| 5 | CH$_2$ | 2-OMe-phenyl | 323.1 (2.85) |
| 6 | CH$_2$ | 3-OMe-phenyl | 323.2 (3.13) |
| 7 | CH$_2$ | 2,4-dimethylphenyl | 321.1 (3.29) |
| 8 | CH$_2$ | 2-fluorophenyl | 311.2 (2.98) |
| 9 | O | 2,4-dichlorophenyl | 363.1 (2.95) |
| 10 | O | 2,4-dimethylphenyl | 323.2 (2.71) |
| 11 | O | 2-OMe-phenyl | 325.1 (2.95) |
| 12 | O | 3-OMe-phenyl | 325.2 (2.54) |
| 13 | O | 3-methyl-4-pyridyl | 364.2 (2.28) |
| 14 | N-Me | 3-methyl-4-pyridyl | 377.1 (1.50) |
| 15 | N-Me | 2,4-dichlorophenyl | 376.1 (2.08) |

TABLE 2
Phenyl substituted furopyridines and furopyrimidines
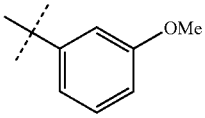
(I)
| Example No. | Ar¹ | Ar² | Y | HPLC/ES-MS [M + H]+ (R$_t$, min) |
|---|---|---|---|---|
| 16 | 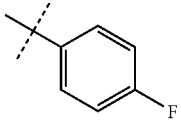 | 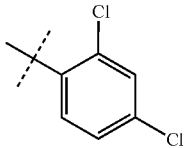 | CH | 363.4 (3.56) |
| 17 | 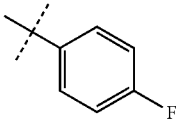 | 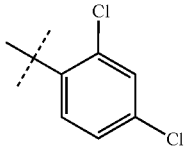 | CH | 401.3 (3.77) |
| 18 | 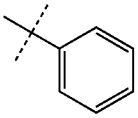 | 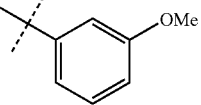 | N | 385.0 (3.92) |
| 19 | 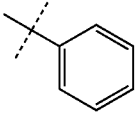 | 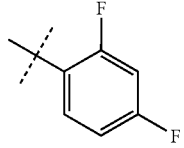 | N | 346.0 (3.40) |
| 20 | 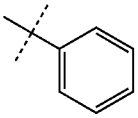 | 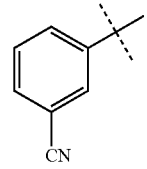 | N | 352.0 (3.45) |
| 21 | 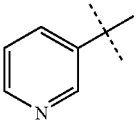 | 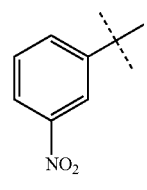 | CH | |
| 22 | 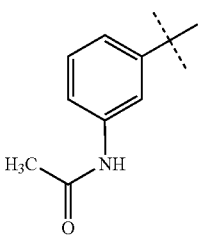 | | CH | |

TABLE 2-continued
Phenyl substituted furopyridines and furopyrimidines
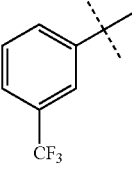
(I)
| Example No. | Ar¹ | Ar² | Y | HPLC/ES-MS [M + H]+ (R$_t$, min) |
|---|---|---|---|---|
| 23 | 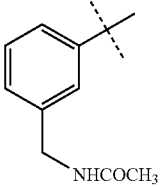 | 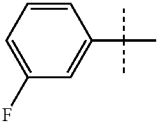 | CH | |
| 24 | 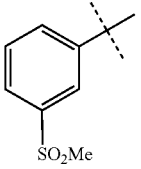 | 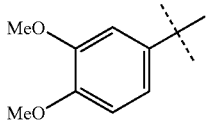 | CH | |
| 25 | 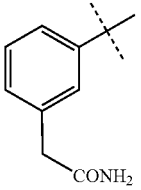 | 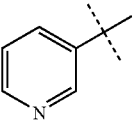 | CH | |
| 26 | 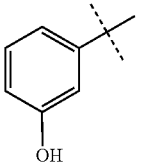 | 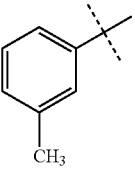 | CH | |
| 27 | 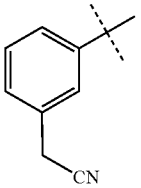 | 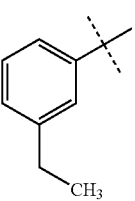 | CH | |
| 28 | 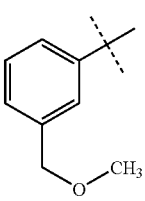 | | CH | |

TABLE 2-continued

Phenyl substituted furopyridines and furopyrimidines (I)

| Example No. | Ar¹ | Ar² | Y | HPLC/ES-MS [M + H]+ ($R_t$, min) |
|---|---|---|---|---|
| 29 | 3-fluorophenyl | 3-methoxyphenyl | CH | |
| 30 | 2,4-dichlorophenyl | 3-(NHSO$_2$CH$_3$-methyl)phenyl | CH | |
| 31 | 2,4-difluorophenyl | 3-nitrophenyl | CH | |
| 32 | 4-nitrophenyl | 3-(ethoxymethyl)phenyl | CH | |
| 33 | 2,4-dimethylphenyl | 3-(aminomethyl)phenyl | CH | |
| 34 | 3-(CF$_3$CH$_2$)phenyl | 3-(trifluoromethyl)phenyl | CH | |
| 35 | 4-methoxyphenyl | 4-(N-methylcarbamoyl)phenyl | CH | |

TABLE 2-continued

Phenyl substituted furopyridines and furopyrimidines (I)

| Example No. | Ar¹ | Ar² | Y | HPLC/ES-MS [M + H]+ ($R_t$, min) |
|---|---|---|---|---|
| 36 | 4-F, 2-Cl phenyl | 3-(pyrrolidin-1-ylcarbonyl)phenyl | CH | |
| 37 | 2-methoxyphenyl | 3-(piperidin-1-ylcarbonyl)phenyl | CH | |
| 38 | 2,5-dimethoxyphenyl | 2,4-difluorophenyl | CH | |
| 39 | 4-isopropylpyridin-3-yl | 3-propanoylphenyl | CH | |
| 40 | 4-F, 2-methoxyphenyl | 3-(morpholin-4-ylcarbonyl)phenyl | CH | |
| 41 | 4-CF₃-pyridin-3-yl | 3-Cl, 4-acetylphenyl | CH | |
| 42 | 2-chlorophenyl | 4-ethylphenyl | CH | |

TABLE 2-continued
Phenyl substituted furopyridines and furopyrimidines
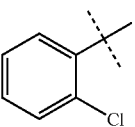
(I)
| Example No. | Ar¹ | Ar² | Y | HPLC/ES-MS [M + H]+ (R_t, min) |
|---|---|---|---|---|
| 43 | 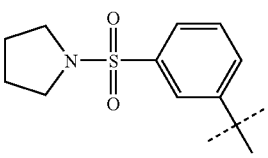 | 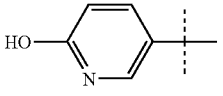 | N | |
| 44 | 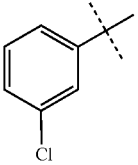 | 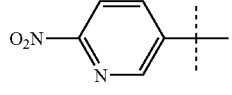 | N | |
| 45 | 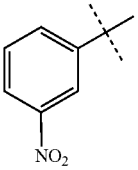 | 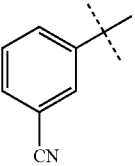 | N | |
| 46 | 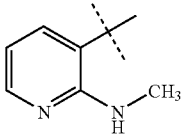 | 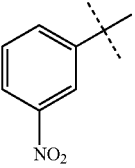 | N | |
| 47 | 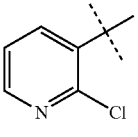 | 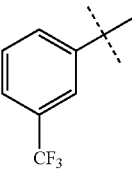 | N | |
| 48 | 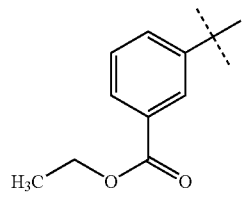 | 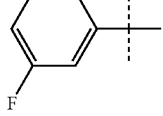 | N | |
| 49 | 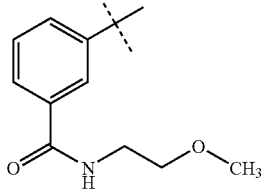 | | N | |

TABLE 2-continued

Phenyl substituted furopyridines and furopyrimidines (I)

| Example No. | Ar¹ | Ar² | Y | HPLC/ES-MS [M + H]+ ($R_t$, min) |
|---|---|---|---|---|
| 50 | 3,4-dimethoxyphenyl | 3-(N-(2-hydroxyethyl)carbamoyl)phenyl | N | |
| 51 | pyridin-3-yl | 3-(N-ethylcarbamoyl)phenyl | N | |
| 52 | 3-ethylphenyl | 3-(N-(2-hydroxyethyl)sulfamoyl)phenyl | N | |
| 53 | 3-fluorophenyl | 3-((3-methoxy-2-hydroxypropyl)amino)phenyl | N | |
| 54 | 2,4-dichlorophenyl | 3-((2,3-dihydroxypropyl)amino)phenyl | N | |

TABLE 2-continued
Phenyl substituted furopyridines and furopyrimidines
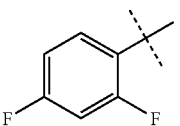
(I)
| Example No. | Ar¹ | Ar² | Y | HPLC/ES-MS [M + H]+ ($R_t$, min) |
|---|---|---|---|---|
| 55 | 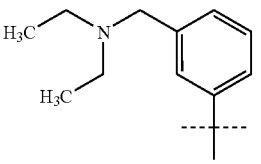 | 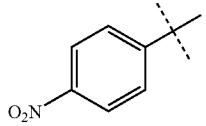 | N | |
| 56 | 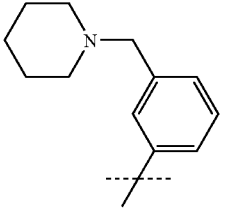 | 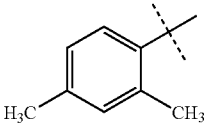 | N | |
| 57 | 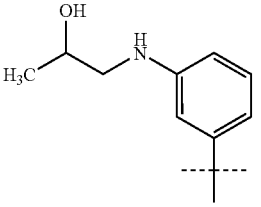 | 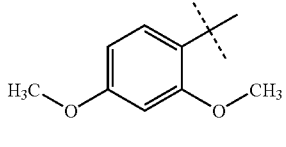 | N | |
| 58 | 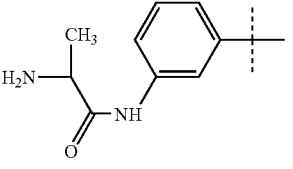 | 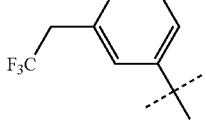 | N | |
| 59 | 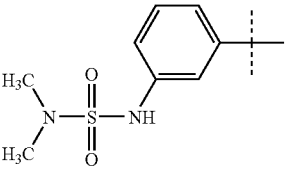 | 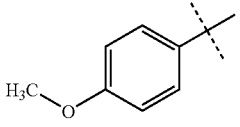 | N | |
| 60 | 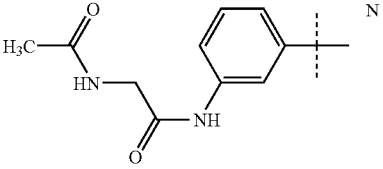 |  | N | |

TABLE 2-continued

Phenyl substituted furopyridines and furopyrimidines (I)

| Example No. | Ar¹ | Ar² | Y | HPLC/ES-MS [M + H]+ ($R_t$, min) |
|---|---|---|---|---|
| 61 | 4-F, 2-Cl-phenyl | 3-(hydroxymethyl)phenyl | N | |

*HPLC-electrospray mass spectra (HPLC ES-MS) data listed in Tables 1 and 2 were obtained using a Hewlett-Packard 1100 HPLC equipped with a quaternary pump, a variable wavelength detector set at 254 nm, a YMC pro C-18 column (2 × 23 mm, 120A), and a Finnigan LCQ ion trap mass spectrometer with electrospray ionization. Spectra were scanned from 120-1200 amu using a variable ion time according to the number of ions in the source. The eluants were A:2%acetonitrile in water with 0.02% TFA and B:2% water in acetonitrile with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes. All compound structures are consistent with the analytical data presented.

The compound structures of Tables 1 and 2 correspond to the IUPAC compound names below.

| Example No. | IUPAC Name* |
|---|---|
| 1 | (3-amino-5,6,7,8-tetrahydrofuro[2,3-b]quinolin-2-yl)-(2,5-dimethoxyphenyl)methanone |
| 2 | (3-amino-5,6,7,8-tetrahydrofuro[2,3-b]quinolin-2-yl)-(4-methyl-3-pyridinyl)methanone |
| 3 | (3-amino-5,6,7,8-tetrahydrofuro[2,3-b]quinolin-2-yl)-(2,4-dichlorophenyl)methanone |
| 4 | (3-amino-5,6,7,8-tetrahydrofuro[2,3-b]quinolin-2-yl)-[4-(trifluoromethyl)-3-pyridinyl]methanone |
| 5 | (3-amino-5,6,7,8-tetrahydrofuro[2,3-b]quinolin-2-yl)-(2-methoxyphenyl)methanone |
| 6 | (3-amino-5,6,7,8-tetrahydrofuro[2,3-b]quinolin-2-yl)(3-methoxyphenyl)methanone |
| 7 | (3-amino-5,6,7,8-tetrahydrofuro[2,3-b]quinolin-2-yl)-(2,4-dimethylphenyl)methanone |
| 8 | (3-amino-5,6,7,8-tetrahydrofuro[2,3-b]quinolin-2-yl)-(2-fluorophenyl)methanone |
| 9 | (3-amino-7,8-dihydro-5H-furo[2,3-b]pyrano[3,4-e]pyridin-2-yl)(2,4-dichlorophenyl)methanone |
| 10 | (3-amino-7,8-dihydro-5H-furo[2,3-b]pyrano[3,4-e]pyridin-2-yl)(2,4-dimethylphenyl)methanone |
| 11 | (3-amino-7,8-dihydro-5H-furo[2,3-b]pyrano[3,4-e]pyridin-2-yl)(2-methoxyphenyl)methanone |
| 12 | (3-amino-7,8-dihydro-5H-furo[2,3-b]pyrano[3,4-e]pyridin-2-yl)(3-methoxyphenyl)methanone |
| 13 | (3-amino-7,8-dihydro-5H-furo[2,3-b]pyrano[3,4-e]pyridin-2-yl)[4-(trifluoromethyl)-3-pyridinyl]methanone |
| 14 | (3-amino-6-methyl-5,6,7,8-tetrahydrofuro[2,3-b]-1,6-naphthyridin-2-yl)[4-(trifluoromethyl)-3-pyridinyl]methanone |
| 15 | (3-amino-6-methyl-5,6,7,8-tetrahydrofuro[2,3-b]-1,6-naphthyridin-2-yl)(2,4-dichlorophenyl)methanone |
| 16 | [3-amino-6-(4-fluorophenyl)furo[2,3-b]pyridin-2-yl](3-methoxyphenyl)methanone |
| 17 | [3-amino-6-(4-fluorophenyl)furo[2,3-b]pyridin-2-yl](2,4-dichlorophenyl)methanone |
| 18 | (5-amino-2-phenyl-furo[2,3-d]pyrimidin-6-yl)-(2,4-dichlorophenyl)-methanone |
| 19 | (5-amino-2-phenyl-furo[2,3-d]pyrimidin-6-yl)-(3-methoxyphenyl)-methanone |
| 20 | (5-amino-2-phenyl-furo[2,3-d]pyrimidin-6-yl)-(2,4-difluorophenyl)-methanone |

*The IUPAC name was obtained using the ACD/ILab Web service

The compounds of this invention may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form, and a substituent on a double bond may be present in either =Z- or =E-form. It is intended that all such configurations (including enantiomers and diastereomers), are included within the scope of the present invention. Preferred compounds are those with the absolute configuration of the compound of this invention which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

Pharmaceutically acceptable salts of these compounds are also within the scope of this invention. The term "pharmaceutically acceptable salt" refers to a relatively non-toxic, inorganic or organic salt of a compound of the present invention. For example, see S. M. Berge, et al. "Pharmaceutical Salts," *J. Pharm. Sci.*, 66: 1-19, 1977.

Representative salts of the compounds of this invention include the conventional non-toxic salts and the quaternary ammonium salts that are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

METHOD OF MAKING THE COMPOUNDS OF THE PRESENT INVENTION

In general, the compounds of this invention may be prepared by standard techniques known in the art, by known processes analogous thereto, and/or by processes disclosed below, using starting materials which are either commercially available or producible according to routine, conventional chemical methods.

The particular process to be utilized in the preparation of the compounds of this invention depends upon the specific compound desired. Such factors as the selection of Y, or the Ar groups, and the specific substituents possible at various locations on the molecule, each play a role in the path to be followed in the preparation of the specific compounds of this invention. Those factors are readily recognized by one of ordinary skill in the art.

The compounds of the present invention are prepared generally according to Reaction Scheme 2 and Reaction Scheme 3.

DEFINITIONS

When the following abbreviations are used herein, they have the following meaning:

| DMF | N,N-dimethylformamide |
| DMSO | dimethylsulfoxide |
| $Et_2O$ | diethyl ether |
| EtOH | ethanol |
| HPLC ES-MS | high performance liquid chromatography-electrospray mass spectroscopy |
| LC/MS | Liquid Chromatography/Mass Spectroscopy |
| MeOH | methanol |
| NMR | Nuclear Magnetic Resonance Spectroscopy |
| RT | retention time (HPLC) |
| $R_f$ | TLC Retention Factor |

-continued

| rt | room temperature |
| TFA | trifluoroacetic acid |
| TLC | thin layer chromatography |

The general method of Reaction Scheme 1 through intermediate (5) is described in Paine, J. B. *J. Heterocycl. Chem.* 1987, 24, 351. By analogy to the Paine method, this method may be used for preparation of the precursor compounds (5) in Reaction Scheme 1 below where X is $CH_2$, O or —N(Me), and Ar represents a substituted phenyl or substituted pyridyl ring.

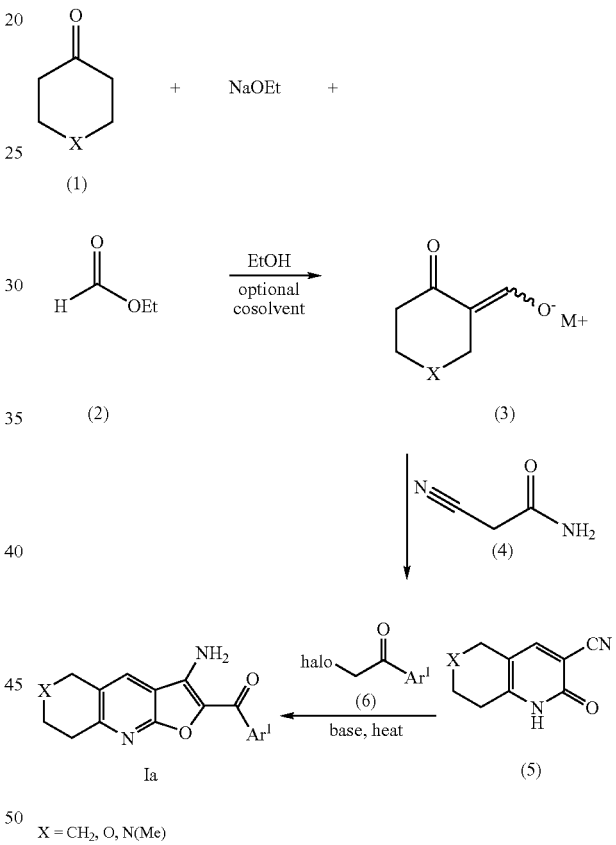

Reaction Scheme 1

$X = CH_2, O, N(Me)$ $Ar^1$ = optionally substituted phenyl or optionally substituted pyridyl Generally, ethanol and ether are mixed with sodium ethoxide and cooled to 0° C. A cyclic ketone (1) and ethyl formate (2) are then added and allowed to react at room temperature to form the hydroxy methylene ketone salt (3), the isolation of which may be facilitated using ether. The salt (3) is then mixed with cyanoacetamide (4) in water and piperidine acetate and refluxed with acetic acid to yield the pyridone (5). The appropriate haloarylketone (6) and potassium carbonate are added to the pyridone (5) in DMF, and the mixture is heated under Argon to yield the compounds Ia in Table 1.

A specific example of this preparation is described next.

PREPARATION OF COMPOUND EXAMPLE 1

(3-amino-5,6,7,8-tetrahydrofuro[2,3-b]quinolin-2-yl)
(2,5-dimethoxyphenyl)methanone (Compound 1a of
Reaction Scheme 1 where X is CH$_2$, and Ar$^1$ is 2,5-
diMeO-Ph-)

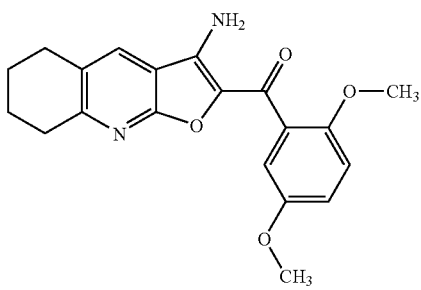

Step 1: Preparation of sodium
(E)-(2-oxocyclohexylidene)methanolate: (3), X is
CH$_2$

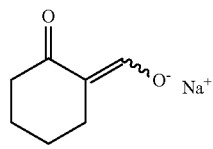

In a 100 mL flask was placed 5 mL of EtOH and 30 mL of Et$_2$O. To this was added NaOEt (1.78 g, 26.1 mmol, 1 equiv.) and the flask was cooled to 0° C. where cyclohexanone (1) (X is CH$_2$, 2.56 g, 26.1 mmol, 1 equiv) was added. After 10 minutes, ethyl formate (2.03 g, 27.4 mmol, 1.05 equiv) was added dropwise, the ice bath was removed, and the mixture was allowed to stir overnight at room temperature.

The mixture was then diluted with enough Et$_2$O to fill the flask and the solids were filtered. The solids were then rinsed with Et$_2$O (100 mL) and dried under high vacuum at 50° C. for 30 minutes to remove any residual Et$_2$O. Isolated 2.57 g (17.3 mmol, 63%) of the desired product as a white solid. $^1$H-NMR (D$_2$O) δ 8.25(s, 1H), 2.03 (q, 4H), 1.51 (m, 2H), 1.42 (m, 2H).

Step 2: Synthesis of 2-hydroxy-5,6,7,8-tetrahydro-3-
quinolinecarbonitrile: (5) X is CH$_2$

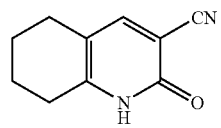

In a 50 mL flask was placed the product of step 1 ((3), X is CH$_2$, 2.0 g, 13.5 mmol, 1 equiv) and cyanoacetamide (4) (1.24 g, 14.7 mmol, 1.09 equiv) in 10 mL of water and 1 mL of piperidine acetate (prepared by adding 7.2 mL of piperidine to a cold solution of 4.2 mL acetic acid in 10.0 mL of water). This was refluxed for 3.5 h at which point 1.5 mL of acetic acid was slowly added to the hot solution. This caused vigorous boiling and effervescence. The mixture was allowed to stir to room temperature overnight.

The precipitated solids were then filtered off and washed with water (30 mL) to provide only 422 mg (2.4 mmol, 18%) of the desired product as a white solid. $^1$H-NMR (DMSO-d$_6$) δ12.26 (s, 1H), 7.87 (s, 1H), 2.55 (t, 2H), 2.41 (t, 2H), 1.65 (m, 4H).

Step 3: Synthesis of the title compound 3-amino-5,6,
7,8-tetrahydrofuro[2,3-b]quinolin-2-yl)(2,5-
dimethoxyphenyl)methanone

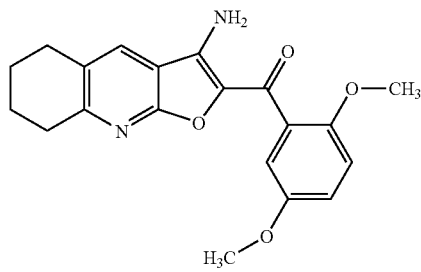

In a 20 mL vial was placed the product of step 2 ((5), X is CH$_2$, 100.0 mg, 0.57 mmol, 1 equiv) and K$_2$CO$_3$ (87.3 mg, 0.63 mmol, 1.1 equiv) in 4 mL of DMF. This was allowed to stir for 5 minutes at 40° C. where 156.2 mg (0.60 mmol, 1.1 equiv.) 2-bromo-1-(2,5-methoxyphenyl)ethanone was added, the vial capped under Argon, and the reaction heated to 80° C. overnight in a sand bath.

The DMF was then removed, the residue dissolved in MeOH, filtered and further purified via HPLC (10-100% MeOH/H2O) to provide 34.7 mg (0.09 mmol, 21%) of the desired compound as a yellow solid. $^1$H-NMR (CD$_3$CN) δ 7.90 (s, 1H), 7.06 (s, 2H), 6.98 (s, 1H), 3.79 (s, 3H), 3.75 (s, 3H), 2.91 (m, 4H), 1.87 (m, 4H); LC/MS R$_t$=2.87 min.; [M+H]$^+$=353.1.

Compounds of Table 1 where X is O or N-methyl can be prepared in a like manner using tetrahydro-4H-pyran-4one or 1-methyl-4-piperidinone for the respective cyclic ketone (1) starting material.

The reference method of Paine cited above also may be used by analogy for preparation of each of the intermediate compounds (9) of Reaction Scheme 2 below that are useful for making the compounds of Formula I where Y is CH.

Reaction Scheme 2

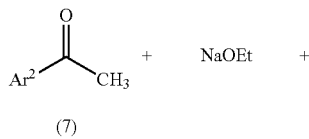

(7)

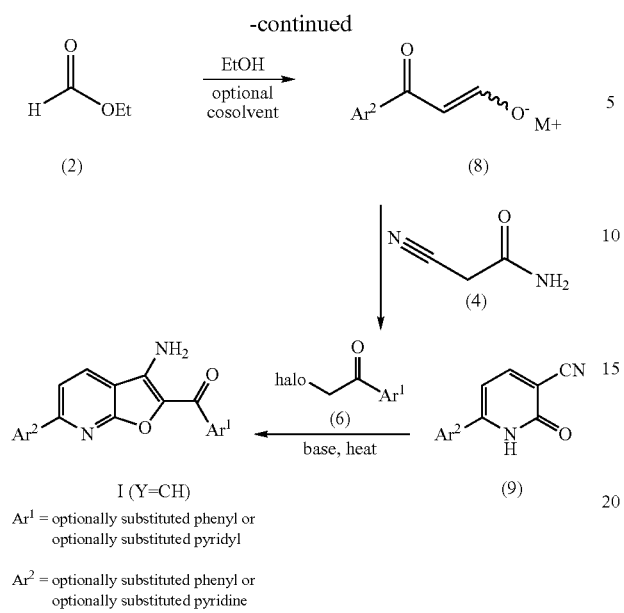

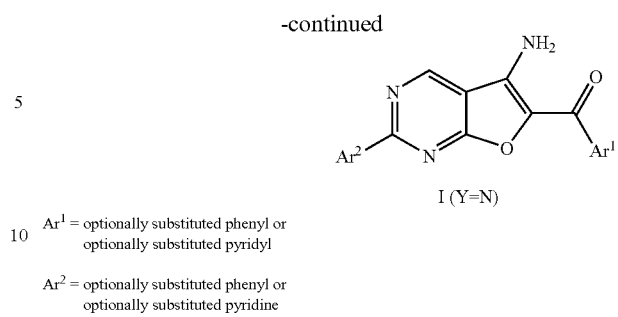

Ar[1] = optionally substituted phenyl or optionally substituted pyridyl

Ar[2] = optionally substituted phenyl or optionally substituted pyridine

Generally, ethanol and ether are mixed with sodium ethoxide and cooled to 0° C. Acetophenone (7) and ethyl formate (2) are then added and allowed to react at room temperature to form the hydroxymethylene ketone salt (8), the isolation of which may be facilitated using ether. The salt (8) is then mixed with cyanoacetamide (4) in water and piperidine acetate and refluxed with acetic acid to yield the pyridone (9). The haloalkylaryl ketone (6) and potassium carbonate were added to the pyridone (9) in DMF, and the mixture was heated under Argon to yield the compounds 1b in Table 2. Specifically, the haloalkylaryl ketones (6) 2-bromo-3'-methoxyacetophenone and 2,2',4'-trichloroacetophenone were used to make the end products Example 16 and Example 17 in Table 2 respectively.

The general method of Reaction Scheme 3 through intermediate (12) is described in *J. Med. Chem.* 1982, 25, 1145. This method is used for preparation of the precursor compounds (12) in Reaction Scheme 3 below where Y is N, Ar[1] represents an optionally substituted phenyl or optionally substituted pyridyl ring and Ar[2] represents an optionally substituted phenyl or optionally substituted pyridine ring.

Reaction Scheme 3

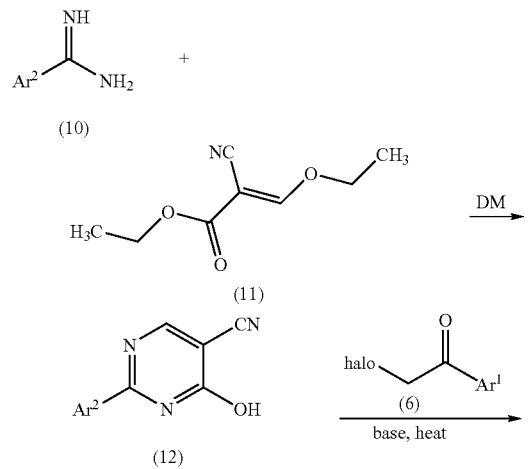

Generally, benzamidine (10) and ethyl(ethoxymethylene)cyanoacetate (11) in DMF was heated under argon to yield the intermediate (12). The purification of which may be facilitated by washing with water and dichloromethane. The haloalkylaryl ketone (6) and sodium hydroxide were added to the intermediate (12) in DMF, and the mixture was heated under argon to yield the compounds I (Y=N) of Table 2.

A specific example of this preparation is described next.

PREPARATION OF COMPOUND EXAMPLE 18

(5-Amino-2-phenyl-furo[2,3-d]pyrimidin-6-yl)-(2,4-dichloro-phenyl)-methanone (Compound I of Reaction Scheme 3 where Y is N. Ar[1] is 2,4-dichloro-Ph- and Ar[2] is phenyl)

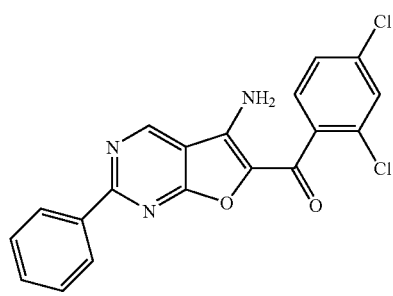

Step 1: Preparation of starting material
4-hydroxy-2-phenyl-pyrimidine-5-carbonitrile (12)

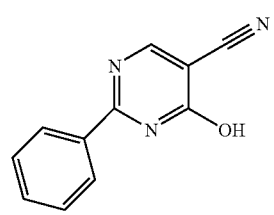

To a stirred solution of benzamidine (1.0 g, 8.32 mmol) in anhydrous DMF (20 mL) was added Ethyl(ethoxymethylene)cyanoacetate (11) (1.41 g, 8.32 mmol, 1.0 equiv) under argon at 0° C. The mixture was stirred at 0° C. for 2 h and increase to 105° C. for 60 h. The reaction mixture was then cooled to ambient temperature. The mixture was extracted with ethyl acetate (2×100 mL). The combined organic extracts were washed with water (1×50 mL) and brine (1×50 mL), dried (Na$_2$SO$_4$), filtered, and evaporated in vacuo. The residue was washed with water (1×60 mL), dichloromethane (1×60 mL) then dried in the vacuum oven to obtain the light yellow solid as product (0.77 g, 47%). $^1$H-NMR (CD$_3$CN) δ 8.25 (s, 1H ), 8.06 (d, 2H ), 7.70 (t, 1H ), 7.61 (t, 2H). MS LC-MS (MH$^+$=198).

Step 2: Preparation of (5-Amino-2-phenyl-furo[2,3-d]pyrimidin-6-yl)-(2,4-dichloro-phenyl)-methanone

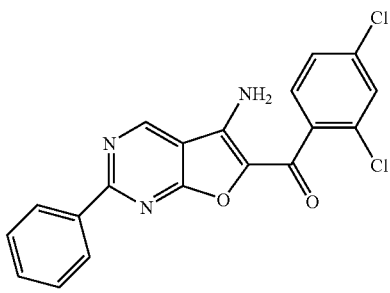

To a stirred solution of 4-hydroxy-2-phenyl-pyrimidine-5-carbonitrile (12) (50 mg, 0.25 mmol, from step 1) and 2-chloro-1-(2,4-dichlorophenyl)ethanone (85 mg, 0.38mmol, 1.5 equiv) in anhydrous N,N-dimethylformamide (1.0 mL) was added NaOH (30.4 mg, 0.76 mmol, 3.0 equiv). The dark brown reaction mixture was stirred at 110° C. for 12 h. The reaction was then poured into ethyl acetate (10 mL) and water (10 mL). Extracted with ethyl acetate (3×10 mL). The organic layer was dried (Na$_2$SO$_4$), filtered, and evaporated in vacuo. The crude product was purified by pre-HPLC to provide 9.1 mg (9.3%) of the desired compound as yellow solid. $^1$H-NMR (CD$_3$CN) δ 9.36 (s, 1H), 8.50 (d, 2H), 7.66 (d, 1H), 7.55 (m, 5H); MS LC-MS (MH$^+$=384/386).

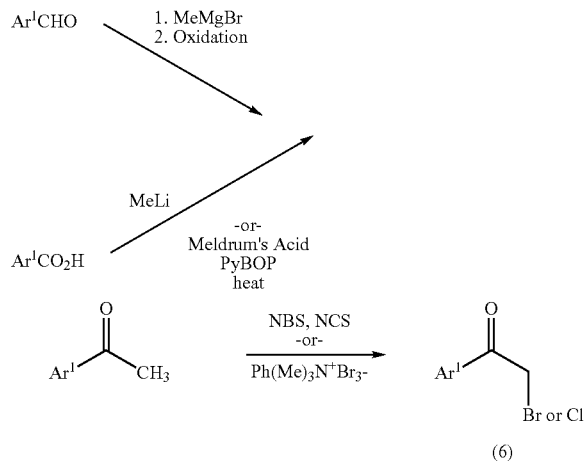

2-Halo-1-arylketones (6) used in this invention are either commercially available or may be prepared as shown in the Reaction Scheme 4. The bromination or chlorination, using standard conditions, of the corresponding aryl methyl ketone which was prepared either from aryl aldehydes or aryl carboxylic acids using conventional organic transformations, gives compound (6). A specific example is described below:

Preparation of 2-chloro-1-[4-(trifluoromethyl)3-pyridinyl]ethanone hydrochloride

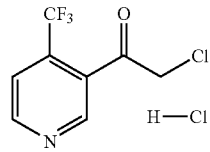

Step 1: In a 250 mL round bottom flask was placed 3.0 g of 4-trifluoronicotinic acid (15.7 mmol, 1 eq) in 100 mL of THF. To this was added 5.3 mL (3.8 g, 37.7 mmol, 2.4 eq) of triethylamine and 9.8 g (18.8 mmol, 1.2 eq) of PyBOP. This was allowed to stir for 10 min at room temperature where 2.7 g of Meldrum's acid (18.8 mmol, 1.2 eq) was added and the reaction allowed stirring at room temperature overnight. (18 h)

At this point, 30 mL of 1 M HCl (aq) was added and the reaction turned immediately from orange to purple. This was then heated at for 18 h gradually turning from purple to yellow. The reaction was then basified with saturated NaHCO$_3$ and extracted with EtOAc (3×200 mL). The combined organic layers were dried, filtered, and evaporated. The residue was purified via BIOTAGE (35% EtOAc/Hex) to provide methyl 4-trifluoromethylnicotinate 1.84 g (62%) of the desired product as a colorless oil. TLC R$_f$=0.57 (50% EtOAc:Hex).

Step 2: In a 100 mL flask was placed 1.84 g (9.7 mmol, 1 eq) of methyl 4-trifluoromethylnicotinate in 25 mL of 1 M HCl in CH$_3$COOH. To this was then added 1.3 g of NCS (9.7 mmol, 1 eq) and the reaction allowed stirring overnight (18 h). The mixture was then transferred to a 500 mL Erlenmeyer flask and to this was added 300 mL of 2 M HCl in Et$_2$O with stirring. This resulted in a white precipitate which was then filtered to provide 1.2 g (49%) of the desired 2-chloro-1-[4trifluoromethyl)-3-pyridinyl]ethanone hydrochloride as a white solid. $^1$H-NMR (DMSO-d$_6$) δ 9.21 (s, 1H), 9.02 (d, 1H), 7.94 (d, 1H), 5.19 (s, 2H).

The aryl amidine compounds (10) were either purchased from commercial sources or prepared from readily available starting material such as aryl nitriles, aryl carboxylic acids and aryl aldehydes by standard organic transformations such as those described in *Bioorganic & Medicinal Chemistry Letters* 2002, 12, 1522-1515, *J. Medicinal Chemistry* 1990, 33 (4), 1230-1241.

Variations of the compounds of the invention can be readily prepared using the processes described above, or by other standard chemical processes known in the art, by employing appropriate starting materials that are readily available and/or are already described herein.

The purification of isomers of a compound of this invention, and the separation of said isomeric mixtures can be accomplished by standard techniques known in the art.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

Composition of the Compounds of this Invention

The compounds of this invention can be utilized to achieve the desired pharmacological effect by administration to a patient in need thereof in an appropriately formulated pharmaceutical composition. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound, or salt thereof, of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, otically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)- Part-1 " *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples-include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Useful pharmaceutical compositions for administration of the compounds according to the present invention can be illustrated as follows:

Sterile IV Solution: A 5 mg/mL solution of the desired compound of this invention is made using sterile, injectable water, and the pH is adjusted if necessary. The solution is diluted for administration to 1-2 mg/mL with sterile 5% dextrose and is administered as an IV infusion over 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds described above, including salts thereof and compositions thereof, to treat mammalian hyper-proliferative disorders. This method comprises administering to a mammal in need thereof, including a human, an amount of a compound of this invention, or a pharmaceutically acceptable salt thereof, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) was demonstrated with the use of in vitro tumor proliferation assays.

The following assay is one of the methods by which compound activity relating to treatment of the disorders identified herein can be determined.

In Vitro Tumor Cell Proliferation Assay

The adherent tumor cell proliferation assay used to test the compounds of the present invention involves a readout called Cell Titre-Glo developed by Promega (Cunningham, B A "A Growing Issue: Cell Proliferation Assays. Modem kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88).

H460 cells (lung carcinoma, purchased from ATCC) are plated in 96-well plates at 3000 cells/well in complete media with 10% Fetal Calf Serum and incubated 24 hours at 37° C. 24 hrs after plating, test compounds are added over a final concentration range of 10 nM to 20 M in serial dilutions a t a final DMSO concentration of 0.2%. Cells are incubated for 72 hours at 37° C. in complete growth media after compound addition. Using the Promega Cell Titer Glo Luminescent assay kit, the number of viable cells/well is determined via measurement of luminescent signal based on amount of intracellular ATP content in cells. Values read at 24-hour incubation are subtracted as Day 0. For determination of IC50's, a linear regression analysis can be used to determine drug concentration which results in a 50% inhibition of cell proliferation using this assay format. Representative compounds of the present invention showed a significant inhibition of tumor cell proliferation in this assay.

Based upon the above and other standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg, and preferably from about 0.01 mg/kg to about 20 mg/kg body weight per day. A unit dosage may contain from about 0.5 mg to about 1500 mg of active ingredient, and can be administered one or more times per day. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The compounds or compositions of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

Optional anti-hyper-proliferative agents which can be added to or administered in conjunction with a compound or composition of this invention include but are not limited to compounds listed on the cancer chemotherapy drug regimens in the 11th Edition of the *Merck Index,* (1996), which is hereby incorporated by reference. These compounds include asparaginase, bleomycin, carboplatin, carmustine, chlorambucil, cisplatin, colaspase, cyclophosphamide, cytarabine, dacarbazine, dactinomycin, daunorubicin, doxorubicin(adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other ant-hyper-proliferative agents suitable for use with this invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparginase, azathioprine, 5-azacytidine cladribine, busulfan, diethylstilbestrol, 2', 2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine. Other anti-hyper-proliferative agents suitable for use with this invention include but are not limited to other anti-cancer agents such as epothilone, irinotecan, raloxifen and topotecan.

It is believed that one skilled in the art, utilizing the preceding information, can utilize the present invention to its fullest extent.

It should be apparent to one of ordinary skill in the art that changes and modifications can be made to this invention without departing from the spirit or scope of the invention as it is set forth herein.

What is claimed is:

1. A compound of Formula I

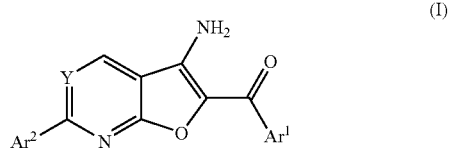

(I)

wherein
  Y is CH;
  $Ar^1$ is phenyl or pyridyl each optionally substituted with 1 or 2 substituents each selected independently from ($C_1$-$C_3$)alkoxy, halo, OH, $CF_3$, CN, $NO_2$ and ($C_1$-$C_3$)alkyl, said alkyl being optionally substituted with $CF_3$;
  $Ar^2$ is phenyl or pyridyl each optionally substituted with 1 or 2 substituents each independently selected from halo, OH, CN, $NO_2$, $CF_3$, ($C_1$-$C_6$)alkoxy, $NR^1R^1$, $S(O)_2R^2$, $C(O)R^3$, and ($C_1$-$C_6$)alkyl optionally substituted with $R^4$;
wherein at least one of $Ar^1$ and $Ar^2$ is not unsubstituted phenyl and wherein when $Ar^1$ or $Ar^2$ is substituted phenyl, said phenyl is not substituted with only 1 ($C_1$-$C_3$)alkyl substituent;

R¹ is selected from H, S(O)₂N[(C₁-C₃)alkyl]₂, S(O)₂NH(C₁-C₃)alkyl, C(O)(C₁-C₃)alkyl where said alkyl is optionally substituted with NR⁵R⁵, and (C₁-C₃)alkyl where said alkyl is optionally substituted with 1 or 2 substituents each selected independently from OH and (C₁-C₃)alkoxy, with the proviso that in any NR¹R¹ group when one R¹ is S(O)₂N[(C₁-C₃)alkyl]₂, S(O)₂NH(C₁-C₃)alkyl or C(O)(C₁-C₃)alkyl then the other R¹ must be other than S(O)₂N[(C₁-C₃)alkyl]₂, S(O)₂NH(C₁-C₃)alkyl or C(O)(C₁-C₃)alkyl;

R² is selected from (C₁-C₃)alkyl, pyrrolidinyl, and NH(C₁-C₃)alkyl where said alkyl is optionally substituted with OH;

R³ is selected from (C₁-C₃)alkyl, (C₁-C₃)alkoxy, morpholinyl, pyrrolidinyl, piperidinyl, and NH(C₁-C₃)alkyl where said alkyl is optionally substituted with OH, (C₁-C₃)alkoxy or N[(C₁-C₃)alkyl]₂;

R⁴ is selected from OH, CN, CF₃, (C₁-C₃)alkoxy, C(O)NR⁵R⁵, NR⁵R⁵, and piperidinyl; and R⁵ is selected from H, (C₁-C₃)alkyl, C(O)(C₁-C₃)alkyl, S(O)₂(C₁-C₃)alkyl and piperidinyl, with the proviso that in any NR⁵R⁵ group when one R⁵ is C(O)(C₁-C₃)alkyl or S(O)₂(C₁-C₃)alkyl, then the other R⁵ must be other than C(O)(C₁-C₃)alkyl or S(O)₂(C₁-C₃)alkyl; and excluding (3-amino-6-phenylfuro[2,3-b]pyridin-2-yl)(4-nitrophenyl)methanone, or a pharmaceutically acceptable salt thereof.

2. A compound of claim 1 wherein Ar¹ is optionally substituted phenyl.

3. A compound of Formula I

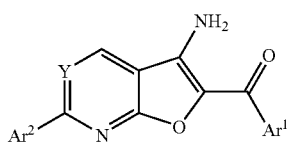

(I)

wherein

Y is CH;

Ar¹ is pyridyl optionally substituted with 1 or 2 substituents each selected independently from (C₁-C₃)alkoxy, halo, OH, CF₃, CN, NO₂ and (C₁-C₃)alkyl, said alkyl being optionally substituted with CF₃;

Ar² is phenyl or pyridyl each optionally substituted with 1 or 2 substituents each independently selected from halo, OH, CN, NO₂, CF₃, (C₁-C₆)alkoxy, NR₁R¹, S(O)₂R², C(O)R³, and (C₁-C₆)alkyl optionally substituted with R⁴;

R¹ is selected from H, S(O)₂N[(C₁-C₃)alkyl]₂, S(O)₂NH(C₁-C₃)alkyl, C(O)(C₁-C₃)alkyl where said alkyl is optionally substituted with NR⁵R⁵, and (C₁-C₃)alkyl where said alkyl is optionally substituted with 1 or 2 substituents each selected independently from OH and (C₁-C₃)alkoxy, with the proviso that in any NR¹R¹ group when one R¹ is S(O)²N[(C₁-C₃)alkyl]², S(O)₂NH(C₁-C₃)alkyl or C(O)(C₁-C₃)alkyl then the other R¹ must be other than S(O)₂N[(C₁-C₃)alkyl]₂, S(O)₂NH(C₁-C₃)alkyl or C(O)(C₁-C₃)alkyl;

R² is selected from (C₁-C₃)alkyl, pyrrolidinyl, and NH(C₁-C₃)alkyl where said alkyl is optionally substituted with OH;

R³ is selected from (C₁-C₃)alkyl, (C₁-C₃)alkoxy, morpholinyl, pyrrolidinyl, piperidinyl, and NH(C₁-C₃)alkyl where said alkyl is optionally substituted with OH, (C₁-C₃)alkoxy or N[(C₁-C₃)alkyl]²;

R⁴ selected from OH, CN, CF₃, (C₁-C₃)alkoxy, C(O)NR⁵R⁵, NR⁵R⁵, and piperidinyl; and R⁵ is selected from H, (C₁-C₃)alkyl, C(O)(C₁-C₃)alkyl, S(O)₂(C₁-C₃)alkyl and piperidinyl, with the proviso that in any NR⁵R⁵ group when one R⁵ is C(O)(C₁-C₃)alkyl or S(O)₂(C₁-C₃)alkyl, then the other R⁵ must be other than C(O)(C₁-C₃)alkyl or S(O)₂(C₁-c₃)alkyl or a pharmaceutically acceptable salt thereof.

4. A compound of claim 1 wherein Ar² is optionally substituted phenyl.

5. A compound of Formula I

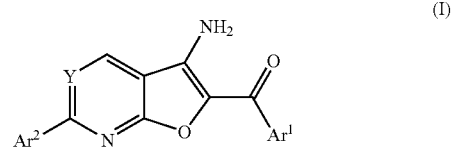

(I)

wherein

Y is CH;

Ar¹ is phenyl or pyridyl each optionally substituted with 1 or 2 substituents each selected independently from (C₁-C₃)alkoxy, halo, OH, CF₃, CN, NO₂ and (C₁-C₃)alkyl, said alkyl being optionally substituted with CF₃;

Ar² is pyridyl optionally substituted with 1 or 2 substituents each independently selected from halo, OH, CN, NO₂, CF₃, (C₁-C₆)alkoxy, NR₁R¹, S(O)₂R², C(O)R³, and (C₁-C₆)alkyl optionally substituted with R⁴;

R¹ is selected from H, S(O)₂N[(C₁-C₃)alkyl]₂, S(O)₂NH(C₁-C₃)alkyl, C(O)(C₁-C₃)alkyl where said alkyl is optionally substituted with NR⁵R⁵, and (C₁-C₃)alkyl where said alkyl is optionally substituted with 1 or 2 substituents each selected independently from OH and (C₁-C₃)alkyl;

with the proviso that in any NR¹R¹ group when one R¹ is S(O)₂N[(C₁-C₃)alkyl]₂, S(O)₂NH(C₁-C₃)alkyl or C(O)(C₁C₃)alkyl then the other R¹ must be other than S(O)₂N[(C₁-C₃)alkyl]₂, S(O)₂NH(C₁-C₃)alkyl or C(O)(C₁-C₃)alkyl;

R² is selected from (C₁-C₃)alkyl, pyrrolidinyl, and NH(C₁-C₃)alkyl where said alkyl is optionally substituted with OH;

R³ is selected from (C₁-C₃)alkyl, (C₁-C₃)alkoxy, morpholinyl, pyrrolidinyl, piperidinyl, and NH(C₁-C₃)alkyl where said alkyl is optionally substituted with OH, (C₁-C₃)alkoxy or N[(C₁-C₃)alkyl]₂;

R⁴ is selected from OH, CN, CF₃, (C₁-C₃)alkoxy, C(O)NR⁵R⁵, NR⁵R⁵, and piperidinyl; and R⁵ is selected from H, (C₁-C₃)alkyl, C(O)(C₁-C₃)alkyl, S(O)₂(C₁-C₃)alkyl and piperidinyl, with the proviso that in any NR⁵R⁵ group when one R⁵ is C(O)(C₁-C₃)alkyl or S(O)₂(C₁-C₃)alkyl, then the other R⁵ must be other than C(O)(C₁-C₃)alkyl or S(O)₂(C₁-C₃)alkyl or a pharmaceutically acceptable salt thereof.

6. A compound of claim 5 wherein Ar¹ is optionally substituted phenyl.

7. A compound of claim 2 wherein Ar² is optionally substituted phenyl.

8. A compound of claim 3 wherein Ar² is optionally substituted phenyl.

9. A compound of claim 3 wherein Ar² is optionally substituted pyridyl.

10. A pharmaceutical composition comprising a compound of Formula I

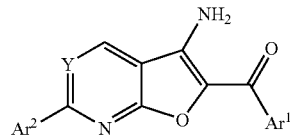

(I)

wherein
Y is CH;
Ar$^1$ is phenyl or pyridyl each optionally substituted with 1 or 2 substituents each selected independently from (C$_1$-C$_3$)alkoxy, halo, OH, CF$_3$, CN, NO$_2$ and (C$_1$-C$_3$)alkyl, said alkyl being optionally substituted with CF$_3$;
Ar$^2$ is phenyl or pyridyl each optionally substituted with 1 or 2 substituents each independently selected from halo, OH, CN, NO$_2$, CF$_3$, (C$_1$-C$_6$)alkoxy, NR$^1$R$^1$, S(O)$_2$R$^2$, C(O)R$^3$, and (C$_1$-C$_6$)alkyl optionally substituted with R$^4$;
wherein at least one of Ar$^1$ and Ar$^2$ is not unsubstituted phenyl and wherein when Ar$^1$ or Ar$^2$ is substituted phenyl, said phenyl is not substituted with only 1 (C$_1$-C$_3$)alkyl substituent;
R$^1$ is selected from H, S(O)$_2$N[(C$_1$-C$_3$)alkyl]$_2$, S(O)$_2$NH(C$_1$-C$_3$)alkyl, C(O)(C$_1$-C$_3$)alkyl where said alkyl is optionally substituted with NR$^5$R$^5$, and (C$_1$-C$_3$)alkyl where said alkyl is optionally substituted with 1 or 2 substituents each selected independently from OH and (C$_1$-C$_3$)alkoxy,
with the proviso that in any NR$^1$R$^1$ group when one R$^1$ is S(O)$_2$N[(C$_1$-C$_3$)alkyl]$_2$, S(O)$_2$NH(C$_1$-C$_3$)alkyl or C(O)(C$_1$-C$_3$)alkyl then the other R$^1$ must be other than S(O)$_2$N[(C$_1$-C$_3$)alkyl]$_2$, S(O)$_2$NH(C$_1$-C$_3$)alkyl or C(O)(C$_1$-C$_3$)alkyl;
R$^2$ is selected from (C$_1$-C$_3$)alkyl, pyrrolidinyl, and NH(C$_1$-C$_3$)alkyl where said alkyl is optionally substituted with OH;
R$^3$ is selected from (C$_1$-C$_3$)alkyl, (C$_1$-C$_3$)alkoxy, morpholinyl, pyrrolidinyl, piperidinyl, and NH(C$_1$-C$_3$)alkyl where said alkyl is optionally substituted with OH, (C$_1$-C$_3$)alkoxy or N[(C$_1$-C$_3$)alkyl]$_2$;
R$^4$ is selected from OH, CN, CF$_3$, (C$_1$-C$_3$)alkoxy, C(O)NR$^5$R$^5$, NR$^5$ R$^5$, and piperidinyl; and
R$^5$ is selected from H, (C$_1$-C$_3$)alkyl, C(O)(C$_1$-C$_3$)alkyl, S(O)$_2$(C$_1$-C$_3$)alkyl and piperidinyl,
with the proviso that in any NR$^5$R$^5$ group when one R$^5$ is C(O)(C$_1$-C$_3$)alkyl or S(O)$_2$(C$_1$-C$_3$)alkyl, then the other R$^5$ must be other than C(O)(C$_1$-C$_3$)alkyl or S(O)$_2$(C$_1$-C$_3$)alkyl; and
excluding, (3-amino-6-phenylfuro[2,3-b]pyridin-2-yl)(4-nitrophenyl)methanone,
or a pharmaceutically acceptable salt thereof,
and a pharmaceutically acceptable carrier.

* * * * *